United States Patent [19]

Hoffmann

[11] 4,444,887
[45] Apr. 24, 1984

[54] PROCESS FOR MAKING HUMAN ANTIBODY PRODUCING B-LYMPHOCYTES

[75] Inventor: Michael K. Hoffmann, New York, N.Y.

[73] Assignee: Sloan-Kettering Institute, New York, N.Y.

[21] Appl. No.: 243,021

[22] Filed: Mar. 12, 1981

Related U.S. Application Data

[63] Continuation-in-part of Ser. No. 101,979, Dec. 10, 1979, abandoned.

[51] Int. Cl.³ .................... C12N 5/00; C12N 5/02; C12P 21/00
[52] U.S. Cl. ..................... 435/240; 435/68; 435/241
[58] Field of Search .................. 435/68, 240, 241

[56] References Cited

PUBLICATIONS

Hoffman et al., Production of Antibody to Sheep Red Blood Cells by Human Tonsil Cells in Vitro–Nature, vol. 243, 1973 (pp. 408–409).

Luzzati et al., Indication of Plaque–Forming Cells in Cultured Human Lymphocytes by Combined Action of Antigen and EB Virus, Nature, vol. 269, 1977 (pp. 419–420).

Heinitz et al., EB Virus–Induced B Lymphocyte Cell Lines Producing Specific Antibody, Nature, vol. 269, 1977 (pp. 420–422).

*Primary Examiner*—David M. Naff
*Attorney, Agent, or Firm*—Felfe & Lynch

[57] ABSTRACT

Antibody producing human B-lymphocytes are produced by a process which comprises culturing human B-lymphocytes in a tissue culture medium in the presence of an antigen; helper signal producing agents comprising monocytes or monocyte conditioned medium containing Interleukin 1 (Il-1), and helper T-lymphocytes or helper T-lymphocyte replacing factor; and human serum; and thereafter recovering the antibody producing cells from the medium.

29 Claims, 8 Drawing Figures

PROCESS FOR MAKING HUMAN ANTIBODY PRODUCING B-LYMPHOCYTES

This invention was made with government support under grant No. CA 17673 awarded by H.E.W. The government has certain rights in this invention.

CROSS REFERENCE TO RELATED APPLICATION

This is a continuation-in-part of co-pending U.S. application Ser. No. 101,979, filed Dec. 10, 1979, now abandoned.

BACKGROUND

This invention relates to a process for making human antibody-producing B lymphocytes in tissue culture. More specifically, this invention relates to the antigen specific induction and regulation of antibody synthesis in cultures of human peripheral blood mononuclear cells. Such antibody producing cells can be used to make hybridomas using cell fusion techniques for producing monoclonal antibodies for therapeutic and diagnostic purposes.

The knowledge of mechanisms that govern the humoral immune response has been greatly advanced by the culture technique, initially developed by Mishell and Dutton for murine spleen cells, which permitted the study of antibody production in virto, Mishell et al., J. Exp. Med. 126: 423, 1967. Application of this technique developed for murine cells to the study of human lymphocytes has been less successful. Human B lymphocytes are obtained from peripheral blood, tonsils, spleens, and lymph nodes. While tonsil and spleen cells have been shown to produce antibodies against certain antigens [sheep red blood cells (SRBC)] in vitro under conditions which are similar to the conditions commonly used in experiments with murine spleen cells, peripheral blood lymphocytes (PBL) did not produce antibodies when cultured and tested in the same way, Hoffman, et al., Nature 243: 408, 1973. As peripheral blood lymphocytes (PBL) represent the only source of lymphocytes which is readily accessible, progress in the study of the humoral immune response in man has been hampered by the lack of technique which permits in vitro sensitization of peripheral blood lymphocytes.

If one disregards the well-established assay that measured the polyclonal production of antibodies which does not depend on antigen, Fauci et al., J. Exp. Med. 144: 674, 1926, success has been reported only by two groups. In the first case, infection with the Epstein-Barr virus (EB virus) was required to enable PBL to produce antibodies in specific response to SRBC or horse red blood cells (HRBC), Luzatti et al., Nature 269: 419, 1977. In the second case, Dosch et al., J. Immunol. 118: 302, 1977, no additional stimulus was used, but the hemolytic plaques in the standard assay has been questioned.

With respect to the use of EB virus, although it stimulates response in Human B lymphocytes, it apparently operates through an extraordinary pathway which cannot be reproduced with more benign mitogens. Furthermore, the usefulness of antibody producing cell lines generated using EB virus, for treatment of human patients is questionable as one would always be in danger of the effect of such viruses. EB virus is known to be tumor producing and also to cause mononucleosis. For these same reasons, laboratory personnel do not want to handle them either.

It has been found that one can use natural pathways of antibody production to generate antibody producing cells from human B lymphocytes. This avoids the need to deal with such extraordinary pathway mitogens as the tumor producing EB virus, with their attendant dangers to personnel working with the virus and patients receiving a possibly contaminated or otherwise dangerous end product. The production of antibody producing cells from Human B lymphocytes (or B-cells) is based on the realization that it is helper cells (macrophages and helper T cells) that support the B cell responses and it is suppressor lymphocytes, present in the B lymphocytes source which suppress or interfere with Human B lymphocytes activation. The effect of the suppressor lymphocytes can be overcome either by their destruction or removal from the Human B lymphocytes or by use of a B cell mitogen to overcome their effect.

SUMMARY

The invention provides a process for producing human antibody producing B lymphocytes in tissue culture using natural antibody producing pathways. The method is a modification of the Mishell-Dutton technique which was developed for the immunization of mouse lymphocytes and not previously applicable to human B lymphocytes.

Human B lymphocytes are obtained from peripheral blood, tonsils, spleens and lymph nodes. These sources normally contain helper cells and suppressor cells.

Basically the method comprises adding human B lymphocytes, to a tissue culture medium along with an antigen, helper cells and homologous serum. To overcome the effects of suppressor cells normally present in the Human B lymphocyte source a proliferation promoter, e.g. a mitogen, may be used and the addition of homologous serum which contains components that activate the suppressor cells, is delayed. Alternatively, the suppressor cells can be removed from the Human B lymphocytes source for example by passing lymphoid cell suspensions over a Sephadex G-1- (Trademark) column, or by serological techniques, e.g. if cytotoxic antibodies are available, by complement dependent cytolysis.

DESCRIPTION OF THE DRAWING

The present invention will be more fully understood from the following description taken in conjunction with the accompanying drawing wherein.

DESCRIPTION

Figure 1A:
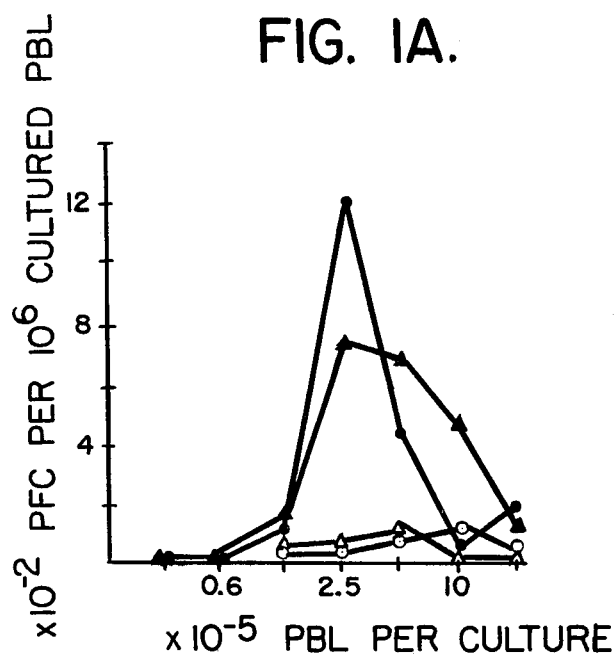
FIGS. 1a and 1b are graphs demonstrating antigen specific sensitization of human PBL as described in Example 5.

The terminology "lymphocyte" and "cell" is used interchangeably in this application—as is usual in the art.

Human B lymphocytes are obtained from peripheral blood, tonsils, spleens or lymph nodes. These sources generally contain varying proportions of helper cells (monocytes and T lymphocytes) and suppressor lymphocytes (suppressor cells).

In accordance with the inventive method, B lymphocytes are stimulated with antigen (for example SRBC). Conversion of antigen-reactive B lymphocytes into antibody-secreting cells requires assistance of monocytes and helper T cells which occur in the lymphoid organs in which Human B lymphocytes are obtained. Monocytes can be substituted with monocyte-conditioned medium (MCM) containing Interleukin 1 (Il-1). (Proc. Natl. Acad. Sci. U.S.A. 77, 1139 (1980)). Helper T cells can be replaced with helper T cells replacing factor which can be obtained in the culture supernatant of activated human T cells.

As noted, lymphoid cell suspensions containing Human B lymphocytes and helper cells (monocytes and helper T cells) contain suppressor cells (or their precursors) which can abrogate antibody formation. The suppressing effect of these cells can be overcome at least partially by use of a B cell mitogen or by their removal prior to culture of lymphoid cells. Either method (or their combination) of overcoming the suppressor cell effect enhances antibody formation substantially.

In general, human lymphoid cell suspensions are cultured according to the method developed by Mishell and Dutton for the sensitization of mouse cells. Two modifications were found necessary to apply this technique to Human B lymphocytes.

(a) Addition of a B cell mitogen (e.g. *Staphylococcus aureus*, Cowan 1 strain). The mitogen can be omitted in suppressor cell depleted lymphoid cell suspensions (e.g. by passing lymphoid cell populations over a Sephadex G-10 (Trademark)) column, or by serological treatment.

(b) Addition of homologous serum. Homologous serum apparently contains components that activate suppressor cells aside from components that are beneficial for antibody responses in vitro. In unseparated cell suspensions serum is therefore added with a delay of 20 hours. However, if a suppressor cell depleted lymphoid cell suspension is used, serum may be added at culture initiation or within 20 hours thereafter.

Finally, if desired, mitogen for T lymphocytes (for example Concanavalin A) may be added 40 hours after culture initiation for the enhancement of helper T cell activity. (Earlier addition of Con A activates suppressor T cells which inhibit antibody formation.)

EXAMPLES 1-8

Lymphoid Cell Suspension B Lymphocyte Source From Which Suppressor Cells Have Not Been Depleted For purposes of carrying out the invention the tissue culture medium is preferably of the Mishell-Dutton type and the cell suspension containing B lymphocytes is plated in concentrations of about $1 \times 10^6$ to $5 \times 10^6$ cell per ml. Human tissue containing B lymphocytes will also contain T lymphocytes which can be removed prior to addition to the culture medium or they can be allowed to remain and their ability to form helper and suppressor cells can be utilized to advantage in the invention by adding a T cell activator to the medium one to two days after the other components are added to the medium. The T cell activator promotes the formation of both helper and suppressor cells but the delayed addition allows the B lymphocyte cells to overcome the effect of the suppressor cells and at the same time to be aided by the helper cells.

It is also possible to cultivate T cells to produce T cell helper factor which can be obtained in T-cell culture supernatant and added to cultures containing B-lymphocytes (Chiorazzi et al, *J. Exp. Med* 149 1543-(1979)).

The addition of human serum is preferably delayed for 16 to 24 hours after the antigen is added to the culture medium. The serum is generally added in concentrations of at least one to ten percent by volume and preferably at least to about five to ten percent by volume.

The proliferation promoter for the B lymphocytes is added. Suitable proliferation promoters are B lymphocyte mitogens such as bacteria, for example *Staphylococcus aereus* (Cowan I strain exposing Ig binding staphylococcus-A protein). Staphylococcus-A is added in concentrations of about 0.03 to about 0.00003 percent, preferably about 0.003 percent, by volume.

Red blood cells are generally used as the antigen such as sheep or burro red blood cells. This system can be extended for the use of other antigens by conjugating these with red blood cells. An example is trinitrophenol which is demonstrated in the examples or other specific antigens such as viruses and the like can be used. Red blood cells associated antigen is generally added to the medium in concentrations of about 0.3 to about 0.0003 percent, preferably about 0.03 percent, by volume.

The use of a differentiation promoter is preferred. A suitable differentiation promoter is Interleukin Il-1 (Il -1), a source of which is described in the examples. It is generally added in the form of monocyte conditioned medium (MCM) in concentrations of about 0.1 to about 30 percent, preferably about 10 percent, by volume.

A T cell activator (mitogen) can be used. A suitable T cell activator is concanavalin A added in a concentration range from 0.3 to 10 $\mu$g/ml preferably at 10 $\mu$g/ml. The addition of this material should be delayed to avoid inhibition of antibody formation.

Reagents: Sheep red blood cells (SRBC), burro red blood cells (BRBC) and horse red blood cells (HRBC) are available commercially from the Colorado Serum Company, Denver, Co. Red cells are conjugated with specific antigens such as 2,4,6-trinitrophenol as described by Kettman et al., *J. Immunol.* 104: 1558, 1970. *Staphylococcus aureus*, Cowan I strain, ATTC 1285 from the American Type Culture Collection (NTCC 8530) is cultured and heat-inactivated as described by Kessler, *J. Immunol.* 115: 1617, 1975. Rabbit anti-SRBC IgG (Cat. No. 678-970) and anti-SRBC IgM (Cat. No. 678-990) are available from Cordis, Miami, Fl. Concanavalin A A grade (lot 610049) is available from Calbiochem, San Diego, CA. Mitomycin C (Cat. No. M-0503) is available from Sigma Chemical Corp., St. Louis, MO.

Preparation of peripheral blood lymphocytes: Heparinized human blood is diluted with an equal volume of culture medium or balanced salt solution (Mishell et al., supra), layered over 15 ml Ficoll-Hypaque (Lymphoprep, Nyegaard and Co., Oslo, Norway) in 50 ml plastic centrifuge tubes (Falcon, No. 2070) and centrifuged for 30 minutes at 400 xg at room temperature. PBL are collected from the interface, washed twice with Eagle's minimal essential medium and resuspended in complete Mishell-Dutton culture medium.

Preparation of monocyte conditioned medium (MCM) containing Il-1: MCM us produced as described by Finelt et al, *Clin. Immunol. Immunopathol.* 12: 281, 1979. 5×10⁶ PBL are incubated at 37° C. for 50 min. in complete Mishell-Dutton medium containing 20% fetal calf serum (FCS) to allow monocytes to adhere to the bottom of the culture dish. The non-adherent cells are subsequently removed by extensive washing and the remaining adherent cells (primarily monocytes) are incubated in serum free Mishell-Dutton culture medium in the presence of 1 μg/ml LPS (S. abortus equi by Dr. Chris Galanos, Freiburg, Germany). Culture supernatants are harvested 24 hr. later, centrifuged for 10 min. at 2,000 rpm, passed through millipore filters (0.45μ) and stored at −70° C. until use. The Il-1 activity of monocyte culture fluids is assessed as described by Finelt et al, *Clin. Immunol. Immunopathol.* 12: 281, 1979.

Cultures: PBL are suspended in complete Mishell-Dutton culture medium which contains in addition 2-mercaptoethanol ($5 \times 10^{-5}$ M). Fetal calf serum is obtained from Microbiological Associates, Walkersville, MD. PBL are placed in different concentrations in 0.1 ml volumes in flat bottom microtiter wells (Costar, Cambridge, MA, No. 3596) and immunized with SRBC (0.03% final concentration) and/or TNP conjugated BRBC (0.03%). Cultures receive also MCM (10%) and heat-inactivated Staph. aureus (0.003% final concentration). Autologous human serum or serum pooled from blood type AB donors is added to a final concentration of 10% 20–24 hr. later. It is not necessary to absorb human serum with antigen to remove SRBC hemolytic activity; however, sera with unusually high hemolytic activity sould be discarded. Cultures are fed daily with 10 μl of a nutritional cocktail, Mishell et al, *J. Exp. Med.* 126: 423, 1967, and harvested on day 5, 6 or 7. Anti-SRBC PFC, Mishell et al, *J. Exp. Med.* 126: 423, 1967, and anti-TNP PFC, Kettman et al, *J. Immunol.* 104: 1558, 1970, are enumerated and expressed as number of PFC per 10⁶ cultured cells.

T cells are isolated from PBL on the basis of their ability to form rosettes with neuraminidase treated SRBC, Weiner et al, *Blood* 42: 939, 1973. Non-rosetting cells, containing B cells and monocytes, are incubated at 37° C. in Mishell-Dutton culture medium containing 20% FCS to allow monocytes to adhere to the culture dish. The non-adherent cells are collected after 60 min., washed and used as a source of B cells.

Cell division is inhibited by subjecting PBL ($5 \times 10^7$/ml) to treatment with mitomycin C (40 γ/ml) in complete medium for 40 min. at 37° C.

Optimal culture conditions for antigen-dependent antibody production: PBL are cultured as described and immunized with SRBC (0.03%) or TNP-conjugated burro red blood cells (BRBC, 0.03%). Added immediately are a 10% suspension of heat-inactivated *S. aureus* (Cowans), 3 λ/ml, and BDF to a final concentration of 10%. Twenty to 24 hr. later human serum, autologous or from a pool of blood type AB donors, is added to a final concentration of 10%.

Antigen dependent generation of antibody forming cells (PFC) depends on the concentration of PBL per culture. In FIG. 1, production of antibody is greatest at a concentration of $1-3 \times 10^5$ PBL per culture. Cultures with less or more PBL produced fewer plaque-forming cells (PFC). The addition of the differentiation promotor (Il-1) is not essential, but it increases the response by a factor of 1.5–8. While antibody is not produced in the absence of human serum, immediate addition is often inhibitory and therefore delayed addition after 16–24 hr. is preferred unless suppressor cells are removed from lymphocyte source. Culture geometry appears to be an important factor; antibody is produced by cultures in flat bottom wells but not by cultures in round bottom wells (FIG. 2). In all experiments, hemolytic plaques are clearly visible and contain a central lymphocyte.

Figure 3:
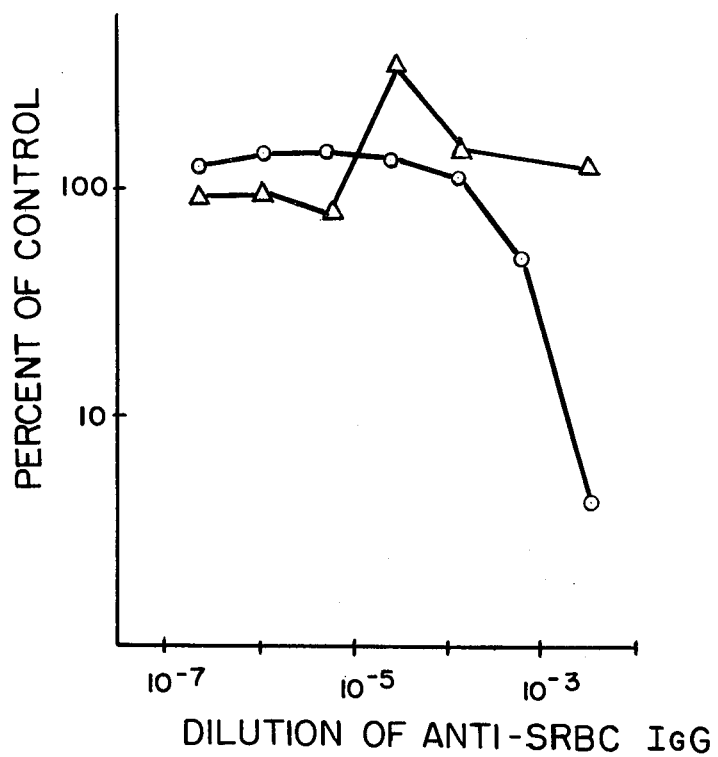
FIG. 3 is a graph relating to the inhibition of response by passively administered antibody as described in Example 7 herein.

Definition of antibody specificity: The specificity of the antibody response is defined in terms of cross-sensitization to unrelated antigens, and inhibition by added antibody. SRBC are found to be a more effective immunogen than the red blood cells of various other species. Burro red blood cells (BRBC), only weakly immunogenic themselves, provided an effective carrier for the hapten TNP. Cultures of human PBL immunized with SRBC or BRBC-TNP generated cells which produce antibody against the immunizing antigen but not the unrelated antigen (Table 1). The production of antibody against SRBC by human PBL in vitro is specifically inhibited by rabbit anti-SRBC Ig. The IgG fraction (FIG. 3) as well as the IgM fraction (Table 2) are inhibitory. By contrast, the anti-TNP response is not inhibited. Anti-SRBC IgM enhances formation of antibody against BRBC and against the TNP-hapten in concentrations in which it inhibited the response to SRBC (Table 2).

Participation of T cells in antibody production: T cells participate as helper cells as well as suppressor cells in the regulation of antibody production in the mouse. To determine if T cells have a helper function in the production of antibody by human PBL, they are separated on the basis of their ability to form rosettes with SRBC, Weiner et al, *Blood* 42: 939, 1973, and the production of antibody by the rosetting fraction (T cells), the non-rosetting fraction (containing B cells) and the combined fractions are tested. While the combined fractions produce anti-TNP antibody, the rosetting fraction and the non-rosetting fraction alone does not (Table 3).

Figure 4A:
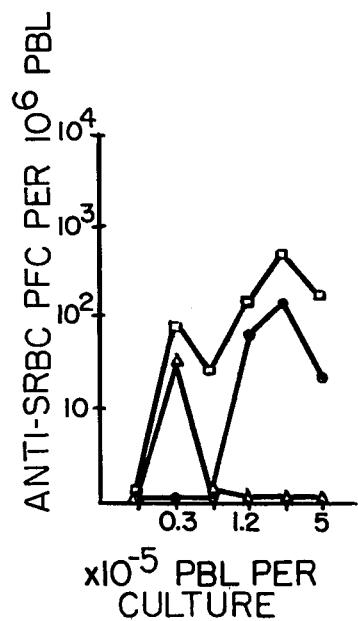
FIGS. 4A, 4B and 4C are graphs relating to the effect of Con A on antibody production as described in Example 8 herein.
Figure 4B:
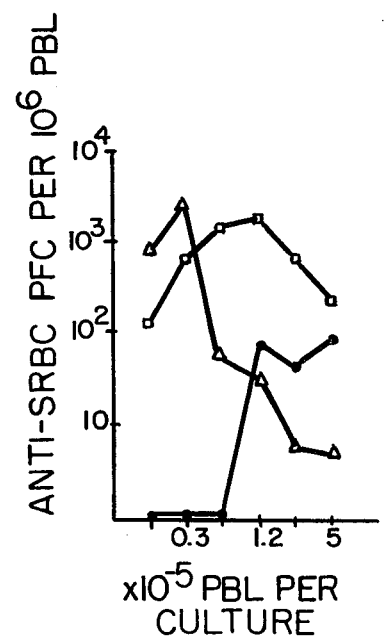
Figure 4C:
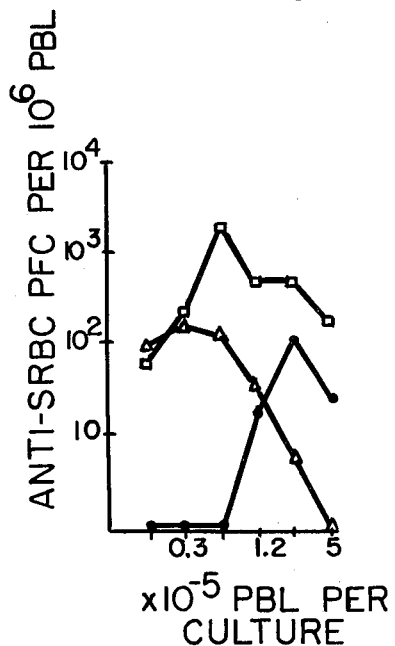

Participation of T cells in the production of antibody by human PBL is shown by testing the effects of concanavalin A (Con A). Con A is known to activate suppressor T cells and helper T cells in the mouse, Dutton, *Transplantation Review,* 26: 39, 1975. Tests indicate that Con A has similar effects on cultures of human peripheral blood lymphocytes (Table 4). Con A inhibits antibody formation when added to the cultures immediately, but enhance antibody formation when added one or two days after sensitization. This is consistent with observations made with cultured murine spleen cells which show that suppressor T cells are effective only in the early phase, Pickel et al, *J. Immunol.* 118: 653, 1977, of culture while Con A stimulated helper T cells [or a T cell replacing factor (TRF) released by them] are most effective when added as late as on the second day of culture, Hoffman et al, *J. Immunol.* 122: 1371, 1979. In addition to being time-dependent, the net effect of Con A depends on the density of murine spleen cells in culture. While antibody production is suppressed by Con A at high cell density, marked stimulation is seen at low cell density, Dutton, *Transplantation Review,* 26: 39, 1975. Similar effects of Con A are shown in cultures of human PBL. In FIG. 4a, human PBL produces antibody against SRBC when cultured at concentrations of $1 \times 10^4$ to $5 \times 10^5$ cells per culture. The response is abrogated by addition of Con A on day 0. By contrast, cultures of lower cell density ($3 \times 10^4$ cells) which did not respond in absence of Con A, produce antibody when Con A is added. The fact that Con A induces antibody formation in cultures of low cell density suggested that these cultures contain adequate numbers of precursor B cells, and that it is an insufficient number of helper T cells which limits the response. To test this we make use of the fact that helper T cells are less sensitive than suppressor T cells to radiation, Dutton, Transplanation Review, 26: 39, 1975, or treatment with mitomycin and add mitomycin treated autologous PBL as a source of helper T cells to the PBL cultures (FIG. 4B). While mitomycin treated PBL alone does not significantly alter the response of PBL, addition of Con A enhances antibody formation markedly as compared with cultures to which mitomycin treated PBL has not been added, particularly in low density cultures. In high density cultures this effect is obscured probably because a larger number of suppressor cells is generated by early addition of Con A in the population that is not treated with mitomycin. This indicates that the production of antibody by PBL is limited in PBL cultures of high cell density by suppressor T cells, and in low density cultures by helper T cells. Allogeneic mitomycin treated PBL are shown to have the same effect as autologous mitomycin treated PBL (FIG. 4C). This indicates that the mixed culture approach is applicable to the dissection of immune defects in patients with primary or secondary immune deficiencies. For example, the ability of mitomycin treated PBL from such patients to generate helper signals in the presence of Con A can be determined, or the ability of their B cells to respond to helper signals provided by mitomycin treated PBL from normal donors can also be determined. Similarly, the presence of suppressor T cells can be demonstrated, and their proportions estimated.

The invention is based on the premise that human PBL contain all cellular elements that are required for the antigen-dependent production of antibody, and fail to produce antibody in response to antigen in vitro because the proportional representation of these cellular elements is different from their representation in the cell populations of tonsil and spleen which produce antibody in vitro, Hoffmann et al, Nature 243: 408, 1973. This is supported by the facts that human PBL can be induced to produce antibody to SRBC in vitro by stimuli which cause a polyclonal response, Fauci et al, J. Exp. Med. 144: 674,1926, and that antigen-dependent production of antibody to SRBC can be induced by subjecting the B lymphocyte population to the additional stimulus of infection with EBV, Luzatti et al, Nature 269: 419, 1977. The addition of S. aureus (which induces proliferation of lymphocytes, Tsuyoshi et al, J. Immunol. 120: 302, 1978) and Il-1 (which supports differentiation of B lymphocytes, Finelt et al, Clin. Immunol. Immunopathol. 12: 281, 1979; Hoffmann et al, J. Immunol, 122: 1371, 1979; Hoffmann et al, J. Immunol. 122: 497, 1978; Hoffmann, Ann. N.Y. Acad. Sci., in 332: 557 (1979) are effective means of supporting the antigen-dependent production of antibody by PBL.

It must be kept in mind that B lymphocytes represent only a small fraction (approximately 8%) of PBL, far out-numbered by the T lymphocyte fraction and of course susceptible to regulation by helper and suppressor T cells. Studies in the mouse indicate that an increase in proportion of T helper and suppressor lymphocytes as it occurs, for example, after stimulation with T cell mitogen, in vitro or with alloantigen, Dutton, Transplantation Review, 26: 39, 1975, changes the balance in favor of suppressor cell activity; increased helper cell activity can often be demonstrated after removal of suppressor T cells (Pickel et al, J. Immunol. 118: 653, 1977; Picket et al, J. Exp. Med. 145: 1169, 1977) unless the spleen cells are cultured at very low density (Dutton, Transplantation Review, 26: 39, 1975, Pickel et al, J. Immunol. 118: 653, 1977); at higher cell density, increased suppressor cell activity completely obscures the increased helper cell activity.

Antibody production by cultures of human PBL at various cell densities are examined. The results are compatible with the concept that the failure of human PBL to produce antibody against erythrocyte antigen in cultures of high cell density is caused by suppressor cells. The mechanism by which suppressor T cells inhibit the production of antibody by B cells is not completely understood. Our observation that cultures of human PBL produce antibody in flat bottom wells but not in round bottom wells where cell contact is closer, supports the view that close proximity among cultured PBL or cell-to-cell contact is necessary for optimal suppressor T cell activity. B cells, when spaced wider in flat bottom wells, are still accessible to soluble mediators released by helper T cells, but do not make contact with suppressor T cells as often as when they are crowded in round bottom wells.

Muchmore et al, J. Immunol. 116: 1016, 1976, have shown that, out of 14 human plasmas examined, three led to the formation of pseudoplaques in cultures of human PBL. These plaques are not the result of active antibody synthesis, but the result of carry-over of aggregates of antibody coated erythrocytes and subsequent release of this antibody in the hemolytic plaque assay. If human plasma used to supplement the culture medium is absorbed with antigen before culture, all pseudoplaque formation is abrogated. The response of human PBL to SRBC and to BRBC-TNP is unaffected by this procedure.

Culture at varying cell density, addition of Con A and addition of mitomycin treated autologous or allogeneic PBL are useful to determine the role played by B cells, helper T cells and suppressor T cells in the production of antibody. The balance is found to be in favor of suppressor T cells in cultures of high cell density, an effect which is accentuated by early addition of Con A. Once the production of antibody has been initiated in such cultures, delayed addition of Con A caused no suppression. In cultures of low cell density, early addition of Con A enhances rather than suppresses the production of antibody. T cell helper function, which does not depend on proliferation, Dutton, Transplantation Review, 26: 39, 1975, is not affected by mitomycin while the development of suppressor T cells and antibody-secreting B cells, which depends on proliferation, Dutton, supra, is inhibited. The mixed culture approach will be of particular importance in dissecting defects in the humoral immune response of patients with primary or secondary immunodeficiency.

EXAMPLE 1

Antigen specificity of antibody generated by human PBL in vitro

PBL are cultured at different cell concentrations in the presence of SRBC, BRBC-TNP or in the absence of antigen. The number of antibody forming cells (PFC) per $10^6$ cultured cells is determined for each concentration and the data shown in Table 1 represents the response of the cell concentration which yielded the highest response. Each value represents the mean of eight cultures.

TABLE 1

| Test | Antigen in Culture | PFC per 10^6 cells | | |
|---|---|---|---|---|
| | | anti-SRBC | anti-BRBC | anti-TNP |
| 1A | SRBC | 425 | 0 | 75 |
| | B-TNP | 27 | 20 | 212 |
| | — | 12 | 0 | 20 |
| 1B | SRBC | 1200 | 0 | 30 |
| | B-TNP | 3 | 0 | 76 |
| | — | 0 | 0 | 26 |
| 1C | SRBC | 384 | 0 | 6 |
| | B-TNP | 120 | 8 | 280 |
| | — | 45 | 0 | 25 |
| 1D | SRBC | 126 | ND | 4 |
| | B-TNP | 5 | ND | 49 |
| | — | 21 | ND | 0 |
| 1E | SRBC | 2300 | ND | 8 |
| | B-TNP | 76 | ND | 59 |
| | — | 58 | ND | 6 |
| 1F | SRBC | 1250 | ND | 136 |
| | B-TNP | 328 | ND | 1430 |
| | — | 168 | ND | 130 |
| 1G | SRBC | 1375 | ND | 245 |
| | B-TNP | 166 | ND | 1002 |
| | — | 284 | ND | 52 |
| 1H | SRBC | 240 | AND | 48 |
| | B-TNP | 56 | ND | 180 |
| | — | 16 | ND | 24 |
| 1I | SRBC | 278 | ND | 76 |
| | B-TNP | 21 | ND | 590 |
| | — | 55 | ND | 42 |

EXAMPLE 2

Inhibition of the anti-SRBC PFC response by rabbit anti-SRBC IgM antibody

PBL are cultured at different cell concentrations ($6 \times 10^4$ to $5 \times 10^5$ per culture) and immunized with SRB and BRBC-TNP. The cell concentration yielding optimal anti-SRBC response are determined in control cultures (no addition of antibody) and the data presented in Table 2 for experimental culture (antibody added) are obtained from cultures containing the same number of PBL. Each value represents the mean of eight cultures.

TABLE 2

| Dilution of rabbit anti-SRBC IgM antibody | PFC per 10^6 cells | | |
|---|---|---|---|
| | anti-SRBC | anti-BRBC | anti-TNP |
| — | 304 | 0 | 140 |
| 1:100 | 30 | 0 | 148 |
| 1:300 | 8 | 40 | 5400 |
| 1:900 | 86 | 148 | 480 |
| 1:2700 | 162 | 12 | 300 |
| 1:8100 | 288 | 0 | 280 |

EXAMPLE 3

Antibody production of human peripheral blood B cells is T cell dependent

PBL, separated in rosetting and non-rosetting fractions based on their ability to bind SRBC are cultured in combinations indicated in Table 3 and sensitized with SRBC and and BRBC-TNP. Antibody forming cell were determined on day 6. Each value represents the mean of eight cultures.

TABLE 3

| Cells in culture ($\times 10^{-5}$) | | PFC per 10^6 cultured cells | |
|---|---|---|---|
| non-rosetting (B cells) | rosetting (T cells) | anti-SRBC | anti-TNP |
| 1.2 | 0 | 0 | 0 |
| 0 | 3 | 110 | 0 |
| 0 | 1 | 185 | 0 |
| 0 | 0.3 | 0 | 0 |
| 1.2 | 3 | 660 | 670 |
| 1.2 | 1 | 490 | 1160 |
| 1.2 | 0.3 | 80 | 210 |

EXAMPLE 4

Effect of Con A on antibody formation by human PBL in vitro

PBL are cultured in a concentration range of $1.5 \times 10^4$ to $5 \times 10^5$ per culture in absence or presence of Con A and sensitized with SRBC. Data is given in Table 4 for the cell concentration that yielded the highest response. Each value represents the mean of eight cultures.

TABLE 4

| Con A (10γ/ml) added day | anti-SRBC PFC per 10^6 cultured cells | | |
|---|---|---|---|
| | day 5 | day 6 | day 7 |
| — | 188 | 370 | 320 |
| 0 | 0 | 64 | 0 |
| 1 | 660 | 2000 | 3600 |
| 2 | 740 | 5400 | 4100 |

EXAMPLE 5

Antigen specific sensitization of human PBL

Figure 1B:
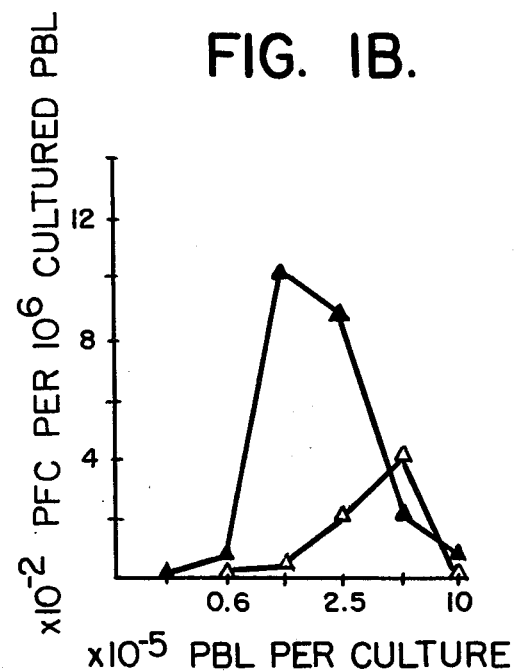
Figure 2A:
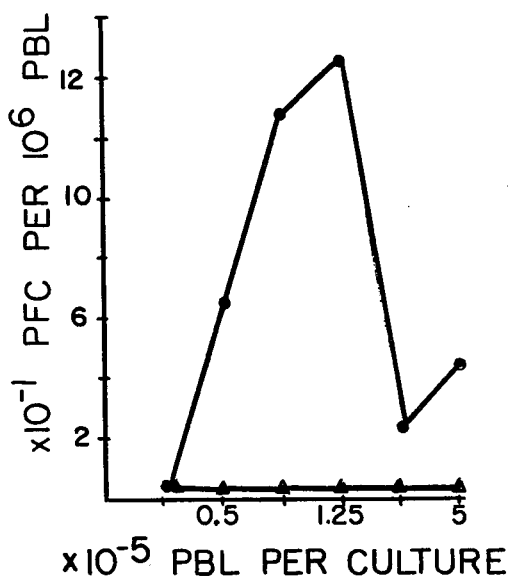
FIGS. 2A and 2B are graphs demonstrating results obtained using different well cultures as described in Example 6 herein.
Figure 2B:
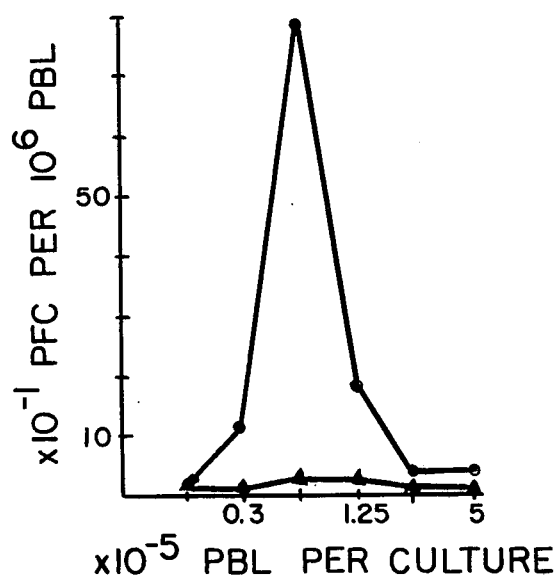

PBL obtained from two donors (A.C., circles and E.W., triangles) are cultured in a concentration range $3 \times 10^4$ to $2 \times 10^6$ cells per culture in presence or absence of antigen (SRBC and BRBC-TNP). PFC formation is determined on day 6. FIG. 1A: anti-SRBC PFC; FIG. 1B: anti-TNP PFC. Closed symbols: antigen added to cultures. Open symbols: no antigen added. The anti-TNP-PFC response is tested only for one donor (E.W.). Each value represents the mean of eight cultures.

EXAMPLE 6

Human PBL fail to generate antigen dependent PFC on round bottom well cultures

PBL are cultured in different concentrations in flat bottom wells (Nunclon, Denmark) o—o or in round bottom wells (Δ—Δ) and immunized with SRBC and BRBC. Anti-SRBC PFC (FIG. 2A) and anti-TNP PFC (FIG. 2B) are determined on day 6. Each value represents the mean of eight cultures.

EXAMPLE 7

Inhibition of the anti-SRBC PFC response by rabbit anti-SRBC IgG

PBL are cultured in different cell concentrations ($5 \times 10^4$ to $5 \times 10^5$ cells/culture) in the presence or absence of anti-SRBC IgG and immunized with SRBC and BRBC-TNP. The cell concentration yielding optimal anti-SRBC response is determined as control value (=100%) on day 6. Data of the experimental cultures (containing anti-SRBC antibody) are shown for cultures containing the same number of cells as control cultures o—o. Anti-TNP PFC are determined in the same cul-

EXAMPLE 8

Effect of Con A on antibody production by PBL

PBL, cultured at different cell densities, are incubated with SRBC alone o—o or received in addition Con A (10 γ/ml) on day 0 △—△ or on day 2 □—□ (FIG. 4A). A second set of cultures (FIG. 4B) is treated identically, except it receives in addition per well $10^5$ mitomycin treated autologus PBL. A third set of cultures (FIG. 4C) receives in addition $10^5$ mitomycin treated PBL per well from another donor. PFC are determined on day 6 from a pool of eight cultures.

EXAMPLES 9–11

Lymphoid Cell Suspension B Lymphocyte Source From Which Suppressor Cells Have Been Depleted The rational for using a non-specific B cell mitogen to support antigen-specific B lymphocytes (B cell) sensitization is to provide antigen-reactive B cells with the strongest possible stimuli so as to enable them to overcome or to escape the inhibitory activity of suppressor cells. To avoid the use of a mitogen (or to enhance its effect) one must reduce or eliminate the effect of suppressor cells in the culture medium. This can be accomplished by removal of suppressor cells by passing, for example, PBM over a Sephadex G-10 (Trademark) column, or serologically by lyzing (when cytotoxic antibodies are available) or by immobilizing suppressor cells.

It has also been found that the advantage of delayed human serum addition to the medium is attenuated, and therefor one may add serum at the start of culturing.

Examples 9, 10 and 11, as summarized in Table 7, show the removal of human suppressor cells using a Sephadex G-10 (Trademark) column facilitates antibody production in the absence of a mitogen. These experiments were accomplished in accordance with the following.

Materials and Methods

Reagents: (Following the reagent preparation for experiments 1-8)

Sheep erythrocytes (SRBC) were obtained from the Colorado Serum Company (Denver, Co.). Staphylococcus aureaus, Cowan I strain (ATCC 1285) was cultured and inactivated as described (Kessler, S. W., "Rapid isolation of antigens from cells with aStaphylococcal protein-A antibody absorbent parameters of the interaction of antibody-antigen complexed with protein A." *J. Immunol.* 115: 1617 (1975)).

Preparation of PBM: (peripheral Blood Mononuclear Cells)

Heparinized human blood was diluted with an equal amount of RPMI 1640 medium (Mishell, R. I., and R. W. Dutton. 1967). Immunization of dissociated spleen cell cultures from normal mice. *J. Exp. Med.* 126: 423, layered over 15 ml of Ficoll/Hypaque (lymphoprep, Nyegaard, Oslo, Norway) in 50 ml plastic centrifuge tubes (Falcon, No. 2070) and centrifuged for 30 min at 400×g at room temperature. PBM were collected from the interface, washed twice with RPMI 1640 medium, and resuspended in complete Mishell-Dutton culture medium (Mishell, R. I., and R. W. Dutton, supra.)

Preparation of Monocytes-Conditioned Medium (MCM) containing IL-1 (Aardeen, L., et al., "Revised nomenclature for antigen-nonspecific T cell proliferation and helper factors," *J. Immunol* 123: 2928 (1979).

MCM was produced as described (Finelt, M., and M. K. Hoffman. "A human monocyte function test: release of B cell differentiation factor," *Clin. Immunol. Immunopathol.* 12: 281 (1979). PBM ($5\times10^6/\mu$) were incubated at 37° C. for 60 min in complete Mishell-Dutton medium containing 20% fetal calf serum to allow monocytes to adhere to the bottom of the culture dish. The non-adherent cells were subsequently removed by extensive washing and the remaining adherent cells (primary monocytes) were incubated in serum-free Mishell-Dutton culture medium in the presence of 1 μg of lipopolysaccharide/ml (derived from Salmonella abortus equi and provided by Chris Galanos, Freiburg, Germany). Culture supernatants were harvested 24 hr later, centrifuged for 10 min at 2000 rpm, passed through Millipore filters (0.45 μm), and stored at $-70°$ C. until used. The IL-1 activity of monocyte culture fluids was assessed as described (Finelt, M., and M. K. Hoffmann, supra.)

Cultures

PBM were suspended in complete Mishell-Dutton culture medium which contained, in addition, 50 μm 2-mercaptoethanol. PBM in serial $Log_2$ dilutions ranging from 5 to $1.25\times10^6$ cells/ml in 0.1 ml volumes were placed in flatbottom microtiter wells (Costar; Cambridge, MA, no. 3596) and exposed to SRBC (0.03% final concentration). Cultures also received MCM (10%) and heat-inactivated S. aureus (0.003% final concentration). Human serum was added to a final concentration of 10% 20–24 hr later (unless indicated otherwise). Cultures were fed daily with 10 μl of a nutritional cocktail (Mishell-Dutton, supra) and harvested on days 5, 6, or 7. Anti-SRBC plaque-forming cells (PFC) (Mishell-Dutton, supra) were enumerated as described and expressed as number of PFC per $10^6$ cultured cells.

Sephadex G-10 fractionation

The following method represents a slight modification of the method described by Ly and Mishell (Ly, I. A., and R. I. Mishell. 1974. Separation of mouse spleen cells by passage through columns of Sephadex G-10. *J. Immunol.*, Metho. 5:239.) Sephadex G-10 (Pharmacia Fine Chemicals, Piscataway, N.J.), is washed five times in five volumes of distilled water and twice in saline. Aliquots (30 ml) of Sephadex G-10 in saline are autoclaved at 110° C. for 30 min and stored at room temperature. Columns are prepared by loading sterile 10 ml plastic syringe barrels with 8 ml of Sephadex G-10 and kept at 37° C. for 60 min. Before addition of PBM cells, each column is washed with 20 ml of balanced salt solution (42° C.), and 5 ml of BSS containing 20% fetal calf serum at 42° C. PBM cells in complete culture medium are kept on ice until used. One milliliter of a PBM cell suspension of $10^8$ cells in RPMI 1640 containing 20% FCS is passed through the column followed by 5 ml of warm BSS containing 5% fetal calf serum. The cell recovery is approximately 50%.

Passage of PBM over Sephadex G-10 columns

Studying the PFC-response in cultures of human peripheral blood cells and being concerned with the possibility that peripheral blood B lymphocytes (amounting to not more than 10% of the PBM cells) may be under particularly strong feedback control by the proportionally larger populations of T cells and monocytes, the PBM cells were filtered over Sephadex G-10 columns with the purpose of removing potential suppressor cells. It was found that this treatment does not significantly influence the responsiveness of PBM cells when cultured under conditions with Human serum added after 20 hr, but it had a marked effect when Human serum was added at the initiation of culture. Early addition of Human serum was inhibitory in unseparated PBM cell cultures (as noted before) but not in cultures of Sephadex G-10 passed PBM cells. A representative experiment is shown in Table 5. These results show that Human serum exerts its inhibitory influence on antibody formation (with early addition) through suppressor cells that can be trapped on Sephadex G-10 columns.

We noted in subsequent experiments that the inhibitory activity of Human serum may differ from donor to donor. An example with two sera, selected to demonstrate this difference is shown in Table 6. When added at the initiation of culture, one serum supported only small PFC-responses in unseparated PBM cultures but was readily supportive in Sephadex G-10 treated PBM cell cultures, whereas the other serum induced similarly high antibody production under both conditions. This observation indicates that the factor in human serum that is involved in the activation of suppressor cells may differ in quantity from donor to donor.

Table 7 shows the generation of antibody forming cells in cultures of Sephadex G-10 treated human PBM in the absence of Staph A bacteria (−) as compared with the presence of Staph A (+) bacteria.

The process of the invention can be used analytically as described above in connection with immune deficiencies. The antibody producing B cells can also be fused to make hybridomas capable of producing monoclonal antibodies. The ability of the present invention to use specific antigens for the sensitization of human B cells makes it now possible to produce monoclonal human antibodies of defined specificity which can be used to diagnostic and therapeutic advantage, Fused cell techniques for making hybridomas are described by Köhler and Milstein in *Nature*, 256, Aug. 7, 1975, pp. 495–97 and *Eur. J. Immunol.*, 1976, 6: 511–19. See also Williams et al, *Cell*, 12: 663–73, November 1977, and Hammerling et al *Cur. Top. Micro and Immunol.*, 81: 100–106, 1978.

TABLE 5

Effect of Early and Delayed Addition of Human Serum on Anitbody Production in Cultures of Unseparated and Sephadex G-10 treated Human PBM

| PBM | anti-SRBC PFC/$10^6$ cells | |
|---|---|---|
| | HS* Day 0 | HS Day 1 |
| unseparated | 116 | 880 |
| Sephadex G-10 | 1200 | 940 |

*Human Serum 10%

TABLE 6

Documentation of an Inhibitory Serum and a Non-Inhibitory Serum as Tested in Cultures of Three Different PBM Donors

| PBM | anti-SRBC PFC/$10^6$ cells | | | |
|---|---|---|---|---|
| | serum SRBC | M.C.* no AG | serum SRBC | E.W.* no AG |
| Exp. 9 | | | | |
| unseparated | 1240 | 43 | 63 | 3 |
| Seph G-10 | 2060 | 21 | 2090 | 7 |
| Exp. 10 | | | | |
| unseparated | 134 | ND** | 0 | ND |
| Seph G-10 | 165 | ND | 490 | ND |
| Exp. 11 | | | | |
| unseparated | 72 | ND | 0 | ND |

TABLE 6-continued

Documentation of an Inhibitory Serum and a Non-Inhibitory Serum as Tested in Cultures of Three Different PBM Donors

| PBM | anti-SRBC PFC/$10^6$ cells | | | |
|---|---|---|---|---|
| | serum SRBC | M.C.* no AG | serum SRBC | E.W.* no AG |
| Seph G-10 | 86 | ND | 540 | ND |

*serum was added at culture start. Both sera were obtained from healthy laboratory personnel. Serum donors and PBM donors were not identical.
**not determined.

TABLE 7

Generation of Antibody Forming Cells in Cultures of Sephandex G-10 Treated Human PBM in the Absence of *Staphylococcus Aureus* Bacteria (Staph A).

| PBM | Anti SRBC PFC/$10^6$ cells | | |
|---|---|---|---|
| | Staph A | SRBC | no Ag |
| Exp. 9 | | | |
| unseparated | + | 860 | 42 |
| unseparated | − | 0 | 0 |
| Seph G-10 | + | 520 | 40 |
| Seph G-10 | − | 185 | 0 |
| Exp. 10 | | | |
| unseparated | + | 786 | 68 |
| unseparated | − | C | 0 |
| Seph-G-10 | + | 1240 | 123 |
| Seph G-10 | − | 215 | 0 |
| Exp. 11 | | | |
| unseparated | + | 329 | 29 |
| unseparated | − | 0 | 0 |
| Seph G-10 | + | 679 | 76 |
| Seph G-10 | − | 170 | 0 |

Human serum was added after culture start.

What is claimed is:

1. Process for making antibody producing human B-lymphocytes which comprises culturing a human lymphoid cell suspension containing human B-lymphocytes and a cell concentration of about $1 \times 10^6$ to $5 \times 10^6$ cells/ml in a tissue culture medium containing:
    (a) 0.3 to 0.003% antigen;
    (b) helper signal producing agents consisting essentially of:
        (i) monocytes or conditioned medium containing interleukin 1 derived from said monocytes in an amount to result in a concentration of 0.1 to 30% and
        (ii) helper T-lymphocytes or helper T-lymphocyte replacing factor obtained from activated T-cells; and
    (c) about 1–10% human serum;
and thereafter recovering the antibody producing human B-Lymphocytes from the medium.

2. The process of claim 1 comprising the additional step of treating the lymphoid cell suspension to remove suppressor cells or their precursors prior to the culturing step.

3. The process of claim 1 wherein said tissue culture medium further comprises a B-lymphocyte mitogen at a concentration of about 0.3 to 0.00003%, as a proliferation promoter.

4. The process of claim 1 wherein said human lymphoid cell suspension contains in addition helper T-lymphocytes and said tissue culture medium comprises a T-lymphocyte mitogen as an activator for the helper T-lymphocytes.

5. The process of claim 1 comprising the additional step of treating the lymphoid cell suspension to remove T-lymphocytes prior to the culturing step.

6. Process of claim 5 wherein said removed T-lymphocytes are cultivated to produce T-lymphocyte helper factor which is isolated and added to the tissue culture medium.

7. Process of claim 1 wherein red blood cells comprise the antigen.

8. Process of claim 7 wherein the red blood cells are conjugated with a specific antigen.

9. Process of claim 1 wherein the antigen is concentration about 0.03%, by volume.

10. Process of claim 4 wherein the T-lymphocyte mitogen is Concanavalin A.

11. Process of claim 3 wherein the B-lymphocyte mitogen is the bacterial mitogen *Staphylococcus aureus* of concentration about 0.003%, by volume.

12. Process of claim 1 wherein said conditioned medium containing Interleukin 1 is in an amount to result in a concentration of about 10%, by volume.

13. Process of claim 1 wherein said human serum is a concentration about 5–10% by volume.

14. Process of claim 10 wherein said T-lymphocyte mitogen is Concanavalin A at a concentration of 0.3 to 10 µg/ml.

15. Process of claim 14 wherein said Concanavalin A is about 10 µg/ml.

16. Process of claim 1 wherein the culture medium is a Mishell-Dutton medium.

17. Process of claim 1 wherein the human lymphoid cell suspension contains in addition suppressor cells or their precursors and further comprises the steps of:
 (a) delaying the addition of human serum to the medium until 16 to 24 hours after culturing has started; and
 (b) adding to the culture medium initially 0.3 to 0.0003% of a B-lymphocyte mitogen as a proliferation promoter.

18. Process of claim 17 wherein said human lymphoid cell suspension contains in addition helper T-lymphocytes, further comprising the step of adding a T-lymphocyte mitogen as an activator for the helper T-lymphocytes.

19. Process of claim 17 comprising the additional step of removing T-lymphocytes from the cell suspension before culturing.

20. Process of claim 19 wherein the removed T-lymphocytes are cultivated to produce T-lymphocyte helper factor which is isolated and added to the B-lymphocyte culture medium.

21. Process of claim 17 wherein red blood cells comprise the antigen.

22. Process of claim 21 wherein the red blood cells are conjugated with a specific antigen.

23. Process of claim 17 wherein the antigen is added to the medium in concentrations of about 0.03% by volume.

24. Process of claim 17 wherein the mitogen is the bacterial mitogen, *Staphylococcus aureus.*

25. Process of claim 17 wherein the proliferation promoter is added to the medium in concentrations of about 0.003%, by volume.

26. Process of claim 17 wherein said conditioned medium containing Interleukin 1 is added to the culture medium in concentrations of about 10% by volume.

27. Process of claim 17 wherein the human serum is added to the culture medium in concentrations of about 5–10% by volume.

28. Process of claim 18 wherein 0.3 to 10 µg/ml Concanavalin A is added as a T-lymphocyte activator.

29. Process of claim 28 wherein the Concanavalin A is added to the medium in concentration of about 10 µg/ml.

* * * * *